United States Patent
Black et al.

(10) Patent No.: US 10,178,865 B2
(45) Date of Patent: *Jan. 15, 2019

(54) INSECT REPELLENT

(71) Applicant: FMC Corporation, Philadelphia, PA (US)

(72) Inventors: Bruce C. Black, Yardley, PA (US); Linda Varanyak, Mercerville, NJ (US); Shreya Sheth, Lawrenceville, NJ (US); Jeffrey P. Blancuzzi, Basking Ridge, NJ (US); Nathan D. Caldwell, Morrisville, PA (US)

(73) Assignee: FMC Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/333,990

(22) Filed: Jul. 17, 2014

(65) Prior Publication Data

US 2015/0025141 A1 Jan. 22, 2015

Related U.S. Application Data

(60) Provisional application No. 61/847,805, filed on Jul. 18, 2013.

(51) Int. Cl.
 *A01N 37/44* (2006.01)
 *A01N 37/06* (2006.01)

(52) U.S. Cl.
 CPC .................................. *A01N 37/44* (2013.01)

(58) Field of Classification Search
 CPC .... A01N 37/44; A01N 2300/00; A01N 37/06; A01N 37/36
 See application file for complete search history.

(56) References Cited

U.S. PATENT DOCUMENTS

| | | | |
|---|---|---|---|
| 2,967,128 A | 1/1961 | Kare | |
| 4,707,496 A * | 11/1987 | Simmons | A61K 8/361 424/DIG. 10 |
| 5,175,175 A | 12/1992 | Wilson et al. | |
| 5,296,226 A | 3/1994 | Askham | |
| 5,354,783 A | 10/1994 | Marin et al. | |
| 5,549,902 A | 8/1996 | Preiser et al. | |
| 5,662,914 A | 9/1997 | Shorey et al. | |
| 6,958,146 B2 | 10/2005 | Askham et al. | |
| 7,867,479 B2 | 1/2011 | Dunham et al. | |
| 8,092,790 B2 | 1/2012 | Dunham et al. | |
| 2010/0310620 A1 * | 12/2010 | Hamilton | A01N 37/02 424/405 |

FOREIGN PATENT DOCUMENTS

| | | |
|---|---|---|
| CA | 2513269 A1 | 8/2004 |
| EP | 0828328 A2 | 3/1998 |
| EP | 0991320 A1 | 4/2000 |
| EP | 1787514 A1 | 5/2007 |
| JP | 62169703 | 10/1993 |
| WO | 2013/059364 A2 | 4/2013 |

OTHER PUBLICATIONS

Heba, Egypt J Agri. Res, 91(2), 2013.*
Farag, 2011, Z. Naturforsch, 66c, 129-135.*
Henn (Alternatives in Insect Management, Circular 1296, Sep. 1989).*
Hovde-Chasin, Pesticide Formulations and Application Systems, 1989.*
Ramsewak et al. (J. Agric. Food Chem. 2001, 49, 5852-5856).*
Maslo Andirobin, katalog bazobuh masel, Jun. 15, 2007. Listed on International Search Report and retrieved from internet at: [www.http://forum.aroma-beauty.ru/index.php?showtopic=3171, p. 1-3].
Colby S.R. "Calculating Synergistic and Antagonistic Responses of Herbicide Combinations", Weeds 1967, 15, pp. 20-22.
Bird Shield® Repellent Concentrate Label, Bird Shield Repellent Corporation, Pullman, WA 99162, www.birdshield.com. 6 pages.
Rollo C.D. et al., "Fatty Acid Necromones for Cockroaches" Naturwissenschaften 81, pp. 409-410 (1994).
Appel, Arthur G, et al., Factors Affecting Coprophagy and Necrophagy by the German Cockroach (*Dictyoptera*: Blattellidae), Proceedings of the Sixth International Conference on Urban Pests, (2008), pp. 139-142.
Pankiw Tanya, "Reducing Honey Bee Defensive Reponses and Social Wasp Colonization with Methyl Anthranilate" Journal of Medical Entomology, vol. 46, No. 4, Jul. 1, 2009. pp. 782-788 XP55074646.
Mullens Bradley A., "Laboratory Trials of Fatty Acids as Repellents or Antifeedants Against Houseflies, Horn Flies and Stable Flies (*Diptera*: Muscidae)" Pest Management Science, vol. 65, No. 12, Dec. 1, 2009, pp. 1360-1366, XP55266533.

* cited by examiner

*Primary Examiner* — Umamaheswari Ramachandran

(57) ABSTRACT

In one aspect, this invention relates to pest repellent composition comprising a fatty acid and an anthranilate ester. In another aspect, this invention relates to a method of repelling pests employing such composition.

15 Claims, No Drawings

INSECT REPELLENT

FIELD OF THE INVENTION

In one aspect, this invention relates to pest repellent composition comprising a fatty acid and an anthranilate ester. In another aspect, this invention relates to a method of repelling pests employing such composition.

BACKGROUND OF THE INVENTION

Insect and acarid pests can cause severe damage to crops and horticultural plants, and may serve as vectors for the transmission of disease for both people and animals. One method of controlling such pests involves the application of chemicals which repels such pests from a given environment. Thus, chemicals such as N,N-diethyl-m-toluamide (also known as DEET) is employed in repellents to protect individuals from mosquitoes, ticks and other similar pests. Other chemicals which affect insect behavior are used to attract or repel insects from a given environment in order to enhance the effectiveness of insecticides, either by attracting insects to the area where insecticides can be more effectively employed, or by repelling them from areas where insecticides are inefficient.

Among the compounds which have been employed to influence insect behavior so as to cause them to move to a different environment is methyl anthranilate. Thus, U.S. Pat. No. 6,958,146 (Askham et al), U.S. Pat. No. 7,867,479 (Dunham et al) and U.S. Pat. No. 8,092,790 (Dunham et al) all disclose the use of methyl anthranilate in the form of the commercial product BIRDSHIELD™ to induce insects to migrate from one environment to another (see, for example, Column 9, lines 26-33 of U.S. Pat. No. 7,867,479).

Anthranilate esters such as methyl anthranilate have long been known to be useful as bird repellents. Thus, U.S. Pat. No. 2,967,128 (Kare) describes the use of such compounds to deter both domestic and wild birds from eating seeds, berries, grains, fruits and the like. Further, such compounds have found to be insect attractants—for example, U.S. Pat. No. 5,296,226 (Askham) states (at Column 3, lines 20-23) that "insects are readily attracted to dimethyl and methyl anthanilate. Crops relatively free of insects were quickly reinfested after being treated with either material." This finding is supported by the disclosures in U.S. Pat. No. 6,958,146 (Askham et al), U.S. Pat. No. 7,867,479 (Dunham et al) and U.S. Pat. No. 8,092,790 (Dunham et al) which show in Table 1 of such publications that sticky traps containing methyl anthranilate quickly became covered with hundreds of insects. The sole exception presented in these patents are house flies (*Musca domesticae*) which we repelled by the use of methyl anthranilate.

Although U.S. Pat. Nos. 6,958,146, 7,867,479 and 8,092,790 all describe BIRDSHIELD™ as being a mixture of methyl anthranilate with a fatty acid, it is noted that the label for such product indicates that it is covered by the claims of U.S. Pat. No. 5,296,226. This patent is directed to bird repellant compositions comprising an anionic surfactant consisting of an alkyl metal salt of a fatty acid; rather than a fatty acid in acid form. According to this publication, the addition of such fatty acid salts results in the formation of micelles of such anthranilate compounds, permitting a more even distribution of such compounds on the surface treated and enhancing their efficacy as bird repellents.

Given that compositions comprising an anthranilate ester and a fatty acid salt will attract most insects and will repel birds, it is completely unexpected that a composition comprising an anthranilate ester and a fatty acid in acid form will effectively repel many insect species as well as acarids, without repelling birds, making them useful for a number of repellent purposes including protecting bird feeders from unwanted insects.

SUMMARY OF THE INVENTION

In one aspect, the present invention is directed to a composition comprising an insect, or acarid repellant amount of a composition comprising: (a) an anthranilate ester; and (b) a fatty acid.

In another aspect this invention is directed to a method of repelling insect and/or acarid pests employing such composition.

DETAILED DESCRIPTION OF THE INVENTION

In one aspect, the present invention is directed to a composition comprising an insect and/or acarid repellant amount of a composition comprising: (a) an anthranilate ester; and (b) a fatty acid.

The anthranilate esters which may be employed include those compounds described in U.S. Pat. No. 2,967,128, which patent is hereby incorporated by reference, and include dimethyl anthranilate, methyl anthranilate, ethyl anthranilate, phenylethyl anthranilate and menthyl anthranilate. Preferred anthranilate esters are dimethyl anthranilate and methyl anthranilate, with methyl anthranilate being particularly preferred.

The fatty acids which may be employed as component (b) include saturated and unsaturated fatty acids containing from 8 to 24 carbon atoms, with fatty acids containing from 13 to 21 carbon atoms being preferred. Illustrative of the fatty acids which may be employed are oleic acid, ricinoleic acid, linoleic acid palmitic acid and stearic acid; with oleic acid being particularly preferred.

Typically, weight ratio of fatty acid to anthranilate ester employed in the compositions of the present invention range from 1:10 to 20:1. Preferably, such ratio will range from 1:5 to 10:1; more preferably such ratio is from 1:1 to 5:1.

The compositions of this invention may further comprise additional additives conventionally employed in agricultural applications, provided that such additives do not react with the fatty acid to convert it into a salt or other form of surfactant. Specifically, the addition of amines such as monoethanolamine, diethanolamine and triethanolamine should be avoided.

Illustrative of further components which may included in the compositions of this invention are antioxidant agents which serve to substantially prolong the desirable action of the fatty acid. Such antioxidant agent(s) protect the chemical and physical integrity of the fatty acid against reaction with oxygen and air pollution alone or in the presence of light. There exists an abundance of suitable antioxidants consisting of commercial and specialty chemicals and their combinations, mixtures and proprietary compositions that are well known to those educated in the art. One particular antioxidant agent is ascorbic acid palmitate. The amount of the antioxidant is preferably from 0.001-0.1% by weight of the total composition.

While the composition can be used neat, i.e. undiluted, it is preferably employed in a diluted form. For example, the composition can be dissolved in a suitable solvent, such as a $C_1$-$C_4$ alcohol (for example, methanol, ethanol, isopropyl alcohol, butanol), a ketone such as acetone, an ester such as ethyl acetate or isopropyl myristate, a refined petroleum distillate solution (for example Sunspray® 6E from Sunoco Inc.) or other non-reactive solvent that will evaporate, preferably in a short period of time, leaving the active mixture of fatty acid and anthranilate ester. The composition can be formulated as an EC with adjuvants, surfactants, stabilizers and preservatives, to be diluted with water for spray application or for application to surfaces such as mopping onto floors, wiping countertops and the like. The repellant compositions can also be formulated as aerosols for application from pressurized containers. The repellant composition can be applied by spraying, painting, or dipping the object to be covered in the composition.

The one aspect, the present invention is directed to a method of repelling insect and/or acarid pests employing the anthranilate ester/fatty acid compositions described above. Such compositions provide effective repellent activity against a number of insect orders including Hymenoptera, including pavement ant, carpenter ant, Argentine ant, little fire ant, ghost ant, cold tolerant ant, wood ant, Asian needle ant, odorus ant, rover ant, fire ant, bigheaded ant, honeybee, carpenter bee, bumble bee, small carpenter bee, European paper wasp, German yellowjacket and bald-faced hornet; Blattodea including German roach, Eastern subterranean termite; Hemiptera including bed bugs and brown marmorated stink bugs; Diptera including *Aedes* and *Anopheles* mosquitoes; Coleoptera including corn rootworm, sawtoothed beetle and confused flour beetle; Siphonaptera including cat flea and Lepidoptra including tobacco budworm. Repellent activity has also been demonstrated against brown dog ticks.

The compositions of the present invention have been shown not to exhibit repellent activity against a number of bird species including hummingbirds, grackles, sparrows, woodpeckers, jays, chickadees, titmouse, wrens, starlings, cardinals, finches, flickers and doves.

The repellent composition of this invention is suitable for excluding pest presence and infestation even in sensitive areas such as food storage and preparation areas, kitchen floors, cabinets, drawers, dining areas and play areas. The repellant composition can be used in other applications such as application in and around buildings (homes, garages, barns, restaurants, wineries, and industrial buildings), electrical boxes, gardens, agricultural fields, golf courses, trash cans, decks and patios and to repel pests at outdoor social events such as outdoor parties, picnics and the like. The composition can be applied onto or incorporated into materials such as paper, cellulose or natural sponges, disposable wipes, cloth, for example, clothing, table cloths, placemats, camping gear (backpacks, tents, tarps or netting) or incorporated into plastics such as trash bags or plastic table coverings. The repellent composition can be sprayed onto bird feeders or onto bird seed to repel competitive pests without repelling birds.

FORMULATION EXAMPLES

Formulation A: The following formulation was prepared to test insect repellency (% by weight): 30% oleic acid, 10% methyl anthranilate and 60% Sunspray 6E (Sunoco Oil Company) were blended until homogenous.

Formulation B: The following formulation was prepared to test insect repellency (% by weight): 9% oleic acid, 3% methyl anthranilate and 88% Sunspray 6E (Sunoco Oil Company) were blended until homogenous.

Formulation C: The following formulation was prepared to test insect repellency (% by weight): 3% oleic acid, 1% methyl anthranilate and 96% Sunspray 6E (Sunoco Oil Company) were blended until homogenous.

Formulation D: The following formulation was prepared to test insect repellency (% by weight): 0.9% oleic acid, 0.3% methyl anthranilate and 98.8% Sunspray 6E (Sunoco Oil Company) were blended until homogenous.

Formulation E: The following formulation was prepared to test insect repellency (% by weight): 0.3% oleic acid, 0.1% methyl anthranilate and 99.6% Sunspray 6E (Sunoco Oil Company) were blended until homogenous.

Formulation F: The following formulation was prepared to test insect repellency (% by weight): 30% oleic acid, 10% methyl anthranilate, 52% methyl laurate, 4% Agnique® ABS 60CB (Calcium Dodecyl Benzene Sulfonate from Cognis Corporation), 2% Agnique® CSD-40 (EO/PO block co-polymer from Cognis Corporation), and 2% Tergitol™ XD (Surfactant from Cow Chemical Corp.). The ingredients were blended until homogenous.

Formulation G: The following formulation was prepared to test insect repellency (% by weight): 10% oleic acid, 10% methyl anthranilate, 3.2% Agnique® ABS 60CB (Calcium Dodecyl Benzene Sulfonate from Cognis Corporation), Agnique® SMO-20 (Sorbitan monooleate from Cognis Corporation), 2.47% Agnique® BP4-3103 (EO/PO block co-polymer from Cognis Corporation), 72.89% Aromatic 100 solvent. The ingredients were blended until homogenous.

Formulation H: The following formulation was prepared to test insect repellency (% by weight): 30% oleic acid, 10% methyl anthranilate, 60% Polyethylene glycol. The ingredients were blended until homogenous.

Formulation I: The following formulation was prepared to test insect repellency (% by weight): 3% oleic acid, 1% methyl anthranilate, 96% Polyethylene glycol. The ingredients were blended until homogenous.

Example 1

Yellowjacket, Hornet and Ant Repellency Using Oleic Acid and Methyl Anthranilate Mixtures The following formulations were prepared to test insect repellency (% by weight):
1) 3% oleic acid, 1% methyl anthranilate, 96% Sunspray 6E (Sunoco Oil Company)
2) 3% oleic acid, 97% Sunspray 6E
3) 1% methyl anthranilate, 99% Sunspray 6E
4) 1% oleic acid, 0.3% methyl anthranilate, 98.7% Sunspray 6E
5) 1% oleic acid, 99% Sunspray 6E
6) 0.3% methyl anthranilate, 99.7% Sunspray 6E Eight six-inch paper plates were baited with 6 mL of honey and two tablespoons of canned mackerel each. Two baited plates were sprayed with 0.25 mL of formulation 1, two were sprayed with formulation 2, two were sprayed with formulation 3 and two were designated as controls and were left untreated. The plates were placed in a wooded area in Ewing Township, New Jersey, USA separated from each other by 25 yards. The plates were observed for two hours during which time German Yellowjacket wasps (*Vespula germanica*), bald-faced hornets (*Vespula maculate*), and several ant species visited and fed from the control plates but avoided all the treated plates. At the end of two hours the number of Black Carpenter ants (*Camponotus pennsylvanicus*) on each plate was counted, the results are summarized in Table 1A and 1B below. Only Carpenter ants were counted as they tended to chase some of the other ant species away. Also, the yellowjackets and hornets were not found on or near the treated plates however, they visited the controls to feed but frequently flew away.

TABLE 1A

Carpenter Ants Found On Baited Plates Test 1

| Formulation Number | Number of Ants on plates |
|---|---|
| 1 | 2 |
| 2 | 77 |
| 3 | 51 |
| Control | 68 |

TABLE 1B

Carpenter Ants Found On Baited Plates Test 2

| Formulation Number | Number of Ants on plates |
|---|---|
| 4 | 5 |
| 5 | 42 |
| 6 | 18 |
| Control | 66 |

The % inhibition of treated plates was calculated using the following formula: % Inhibition=(ants on control plates−ants on treated plates/ants on control plates)×100. The % inhibition for each formulation is summarized in Table 2 below.

TABLE 2

% Inhibition

| Formulation Number | Number of Ants on plates |
|---|---|
| 1 | 97% |
| 2 | −13% |
| 3 | 25% |
| 4 | 92% |
| 5 | 36% |
| 6 | 73% |

The presence of a synergistic effect between the two active ingredients is established with the aid of the Colby equation (see Colby, S. R., "Calculating Synergistic and Antagonistic Responses of Herbicide Combinations", *Weeds* 1967, 15, pg 20-22): $E=X+Y-(XY/100)$.

Using the method of Colby, the presence of a synergistic interaction between two active ingredients is established by first calculating the expected activity, 'E', of the mixture based on activities of the two components applied alone. If 'E' is lower than the observed activity, synergy is present. In the equation above, 'X' is the percentage control observed when oleic acid applied alone at rate 'x'. The 'Y' term is percentage control observed when methyl anthranilate applied alone at rate 'y'. The equation calculates 'E', the expected activity of the mixture of 'X' at rate 'x' with 'Y' at rate 'y' if their effects are strictly additive and no interaction has occurred.

For Test 1 the calculated "E" value is 15% whereas the actual value is 97%, an improvement of 82% over the expected additive effect. The "E" value for Test 2 is 83% whereas the actual value is 92%, an improvement of 9% over the expected value. Both tests indicate a synergistic effect is obtained using a 3:1 ratio of oleic acid and methyl anthranilate.

Example 2

Bee Repellency Using an Oleic Acid and Methyl Anthranilate Mixture

Two six-inch paper plates were baited with 6 mL of honey each. One of the baited plates was sprayed with about 0.25 mL of Formulation A and one was designated as a control and was untreated. The plates were placed in a wooded area in Yardley, Pa. separated from each other by one foot, about 35 yards from the hive. The plates were observed for two hours during which time over 70 honey bees (*Apis mellifera*) visited and fed from the control plate but no bees neared the treated plate. At the end of two hours the number of honey bees on each plate was counted, the control had 14 bees and the treated plate had none.

Example 3

Insect Repellency Using an Oleic Acid and Methyl Anthranilate Mixture

Two six-inch paper plates were baited with a tablespoon of canned cat food each. One of the baited plates was sprayed with 0.302 grams of Formulation F and one was designated as a control and was untreated. Honey (25 mL) was diluted with 75 mL of warm tap water and the mixture was stirred to form a homogenous solution. The plates were placed in a wooded area in Ewing Township, New Jersey, USA separated from each other by 5 yards. Fifty mL of the diluted honey solution was poured onto each test plate. The plates were observed at two, four and six hours for insects. At the end of two hours the number of insects on each plate was counted, the control had 7 ants and 6 German Yellowjacket wasps, the treated plate had none. At the four hour check the bait on the control plate was totally consumed and the bait was replaced, the treated plate had two ants and a dead house fly (these were removed). At six hours the control plate had 8 German Yellowjacket wasps and 4 ants where the test plate had no insects on it.

Example 4

Wasp Repellency Using an Oleic Acid and Methyl Anthranilate Mixture

An eight inch paper plate was baited with an aqueous 25% honey solution and was placed on a cement block in a wooded area in Ewing Township, New Jersey USA. After four hours about 50 German Yellowjacket wasps were actively flying around and feeding from the baited plate. When five to eight wasps were feeding on the bait, about 5 mL of Formulation F was applied as a mist over the plate and the area adjacent to the plate using a hand-pump spray bottle. All Yellowjacket wasps evacuated the plate and vicinity. One wasp died by direct contact with the spray. Many of the wasps approached to within about six inches of the treated area but no closer. Within ten minutes, all wasps were gone. After one hour one wasp was flying around the plate but did not land on or near the plate. No additional insect species were observed on or near the plate post treatment.

Example 5

European Paper Wasp Repellency Using an Oleic Acid and Methyl Anthranilate Mixture An active European paper wasp (*Polistes* sp) nest was located outside an office building in Ewing, N.J., USA having over 70 cells and about 10 wasps tending the nest.

Formulation A was poured into a 32 ounce Zep® spray bottle with the nozzle adjusted to deliver a fine mist and the nest was sprayed using two pumps from the spray bottle. There were four wasps on the nest at the time of application and were killed instantly (these were removed from the nest). Within minutes three wasps were observed returning to the nest however they were repelled and would not land on the nest and finally abandoned the nest after several attempts to land. After 16 hours, two weeks and four weeks the nest was still abandoned.

Example 6

Insect Repellency Using an Oleic Acid and Methyl Anthranilate Mixture

Formulation A was poured into a plastic spray bottle and was sprayed onto 20 eight inch paper plates, one squeeze of the pump trigger per plate. The treated plates were weighed and found that about 0.22 gm to about 0.24 gram was applied per plate. Ten treated plates were placed randomly on the ground on a farm in Sparks, Ga., USA and ten control (untreated) plates were placed on the ground about 3 feet from the treated plates. Ten treated plates were placed about 4 feet from active Red imported fire ant mounds and ten control plates were placed near the same mounds no closer than 3 feet from the treated plates. Each plate received approximately 15 mL of an aqueous 25% honey solution. The test plates were observed for four hours.

Of the randomly placed treated plates seven had no insect activity, one had two species of fly (Black fungus gnat (*Bradysia* sp), and Long-legged fly (*Dolichopus* sp), all dead) one had a wood cockroach (dead) (*Parcoblatta pennsylvanica*) and one had one Black fungus gnat (dead). The control plates had several ant species as well as Black fungus gnat, Long-legged fly, hover fly (*Syrphidae* sp), Chalcid wasp (*Chalcidoidea* sp), honey bee and cockroach. None of the insects on the control plates were dead.

Of the treated plates placed near active Red imported fire ant (*Solenopsis invicta*) mounds, none had any insect on or near them. Fifty percent of the control plates had active fire ant feeding within 15 minutes and 100% of the control plates had active fire ant feeding within 30 minutes. None of the treated plates had active fire ant feeding for four hours.

In a separate trial, plates treated with methyl anthranilate only (about 100 mg), baited with a honey solution, placed within 4 feet of fire ant mounds did not deter fire ants from feeding upon these treated plates.

A number of ant species were identified as feeding on control plates but not on the treated plates in the above examples 2, 3, 4 and 6 and in other tests conducted similarly to the above examples. These Genera include the following Formicidae family:
1) *Tetramorium*—Pavement ant
2) *Camponotus*—Carpenter ant
3) *Wasmannia*—Little fire ant
4) *Tapinoma*—Ghost ant
5) *Stenamma*—Cold tolerant ant
6) *Formica*—Wood ant
7) *Pachycondyla*—Asian needle ant
8) *Dorymyrmex*—Odorus ant
9) *Brachymyrmex*—Rover ant
10) *Solenopsis*—Fire ant
11) *Pheidole*—Bigheaded ant
12) *Linepithema*—Argentine ant Example 7

Insect Repellency Using an Oleic Acid and Methyl Anthranilate Mixture

A plastic hummingbird feeder was filled with hummingbird food solution and was hung in a residential back yard and observed for two hours. The feeder was visited by 17 honey bees and 3 humming birds, all of which fed from the feeder. The feeder was sprayed with Formulation A using a plastic spray bottle and was re-hung. The treated feeder was observed for two hours and in the first 30 minutes about 25 honey bees flew close to the feeder, two coming within one inch but not landing. After 30 minutes, bees completely abandoned the feeder. During the two hour period there were 4 feeding hummingbird visits indicating that hummingbirds are not affected by the oleic acid/methyl anthranilate mixture.

Example 8

Insect Repellency Using an Oleic Acid and Methyl Anthranilate Mixture at a Staged Picnic Setting A picnic setting was prepared in a wooded area in Ewing, N.J., with two gallon pails, one treated and one non-treated (trash buckets), paper placemats with paper plates on them atop of a sheet of plywood placed on the ground, one placemat treated and on non-treated (picnic table setting) and open plastic trash bags, one treated and one non-treated (simulated garbage bags). The inside of one of the two gallon pails was sprayed with Formulation A. A paper cup was placed on the bottom of the pail and a paper plate baited with 10 mL of honey diluted in 20 mL of tap water was placed on the cup. The control pail was baited in the same way. One mL of Formulation A was wiped onto a paper placemat, approximately 12 inches by 15 inches. The treated placemat and a control placemat (no treatment) were placed on top of a sheet of plywood set on the ground separated by about 4 feet. A paper plate baited with a blend of canned cat food and honey was placed in the center of each placemat. The inside of a one gallon Ziploc® plastic storage bag was sprayed with about 0.5 mL of Formulation A to which about 50 mL of a dilute aqueous 25% honey solution was added. The bag was suspended from a tree branch about 4 feet from the ground using a metal coat hanger as a frame to hold the bag in an open position. A similar untreated bag was prepared as a control and placed about 10 yards apart. The site was observed for insect activity at 2 and 4 hours after set up. The observations are summarized in the Table below.

| Insect Observations 2 and 4 Hours After Picnic Test Set Up | | |
|---|---|---|
| | 2 Hour | 4 Hour |
| Plate in pail | | |
| Untreated | 10 wasps* | All bait consumed |
| Treated | No insects | 1 wasp |
| Plate on placemat | | |
| Untreated | 10 ants, no wasps | 16 carpenter ants, 1 wasp |
| Treated | 1 carpenter ant, no wasps | 4 carpenter ants, 1 wasp |
| Plastic storage bag | | |
| Untreated | 6 wasps | 6 wasps |
| Treated | No insects | No insects |

*Wasps observed were German Yellowjacket wasps.

The data from this test indicates that oleic acid/methyl anthranilate mixtures can be used to repel insects from a picnic or outdoor social setting.

Example 9

Insect Repellency Using Oleic Acid and Methyl Anthranilate Mixtures

Paper plates were baited with two tablespoons of canned cat food and about 5 mL of honey solution. The plates were over-sprayed with test Formulations A, B, C, D and E, two plates per formulation. Two baited plates were left untreated as controls. The baited plates were placed in a wooded area of Ewing, N.J. After two hours the plates were observed for insect activity. The observations are summarized in the table below. Although German Yellowjacket wasps were drawn to the control plates, none were seen on any of the treated plates.

| Summary of Carpenter Ant observations on Treated and Untreated Baited Plates | |
| --- | --- |
| Formulation Used | Average Number of Carpenter Ants (*Camponotus* sp) Observed |
| A | 0 |
| B | 14 |
| C | 29 |
| D | 33 |
| E | 89 |
| Control | 62 |

This data indicated that all rates of oleic acid and methyl anthranilate tested were repellant to wasps and the mixtures containing 40%, 10%, 4% and 1.2% of the oleic acid/methyl anthranilate ingredients exhibited repellency to carpenter ants.

Example 10

Insect Repellency Field Test Using Oleic Acid and Methyl Anthranilate Mixture

Formulation F (34.9 grams, was sprayed onto a 3 foot by 3 foot area of blooming goldenrod. One replicate test was also performed. Two untreated 3 foot by 3 foot areas of blooming goldenrod were included in this test. The treated and untreated areas were observed for one hour after treatment and also between 2 and 3 hours after treatment. The insects observed in these test areas are summarized in the table below.

| Summary of Insects Observed in or on Blooming Goldenrod | |
| --- | --- |
| Control Area | Treated Area |
| Hour 0-1 | Hour 0-1 |
| 8 Honeybees; 5 flies (Mixed Species); 1 Potter Wasp (*Eumeninae fratemus*); 1 Tawny Skipper Moth (*Polites themistocles*) | No Insect Activity |
| Hour 2-3 | Hour 2-3 |
| 7 Honeybees; 6 flies (Mixed Species); 2 Tawny Skipper Moths; 1 Corn Rootworm Beetle; 1 Jumping Spider (*Salticus* sp) | No Insect Activity |

This data indicated that the oleic acid and methyl anthranilate mixture has a repelling effect when sprayed onto blooming goldenrod.

Example 11

Honey Bee Repellency Using Oleic Acid and Methyl Anthranilate Mixtures

Ten paper plates were baited with about 5 mL of honey. Formulations A, B, C, D and E were diluted with tap water 1 part formulation to 10 parts of water. Baited plates were over-sprayed with the diluted formulations, one plate per formulation. A treated and untreated plate was placed on a table about 35 yards from a honeybee hive. Each test rate was observed for a period of time and observations of honeybees on the test plates made every few minutes. After each observation the plates positions were switched to eliminate positional effects caused by the bees favoring certain locations of the plates. The lowest rate was tested first (Formulation E) and the highest rate (Formulation A) was tested last. The summary of honeybee on each plate is summarized in the table below.

| Honeybees Observed on Baited Test Plates | | | |
| --- | --- | --- | --- |
| Test Formulation | Elapsed Time From Start (minutes) | Number of Honeybees on Control Plate | Number of Honeybees on Test Plate |
| E | 5 | 6 | 0 |
| E | 63 | 19 | 0 |
| E | 64 | 7 | 2 |
| E | 67 | 7 | 7 |
| E | 70 | 7 | 10 |
| E | 89 | 0 | 15 |
| E | 94 | 3 | 21 |
| E | 100 | 19 | 1 |
| D | 5 | 3 | 1 |
| D | 10 | 10 | 2 |
| D | 42 | 2 | 4 |
| D | 55 | 4 | 5 |
| D | 69 | 9 | 6 |
| D | 90 | 12 | 5 |
| D | 122 | 10 | 6 |
| D | 137 | 12 | 8 |
| C | 5 | 0 | 3 |
| C | 14 | 9 | 6 |
| C | 24 | 8 | 5 |
| C | 39 | 12 | 12 |
| B | 5 | 0 | 0 |
| B | 9 | 4 | 0 |
| B | 30 | 13 | 2 |
| B | 40 | 9 | 1 |
| B | 49 | 16 | 1 |
| B | 54 | 12 | 0 |
| A | 5 | 0 | 0 |
| A | 10 | 14 | 0 |
| A | 11 | 19 | 1 |
| A | 14 | 19 | 0 |
| A | 16 | 22 | 0 |
| A | 24 | 18 | 0 |
| A | 27 | 21 | 0 |
| A | 36 | 17 | 1 |
| A | 43 | 20 | 0 |

As can be seen from the above data, the test solutions repelled honeybees from treated baited test plates.

Example 12

Eastern Subterranean Termite Repellency

A termite test arena was prepared by placing a piece of clear Plexiglas (about 8 inches by 12 inches) flat on a table (bottom piece of Plexiglas). Three square pieces of corrugated cardboard (about 2 inches by 2 inches) were laid on the bottom Plexiglas, one centered at the bottom edge and one at each top edge right and left side, with the grooves running vertical. These cardboard pieces will provide food for the termites during the test. Water, 30 grams, was added to 300 grams of natural play sand and the mixture stirred well to thoroughly incorporate the water. A piece of Plexiglas, approximately 1 inch wide was placed on the bottom piece of Plexiglas touching the lower edges of the cardboard pieces located at the top right and left edges. The wetted sand was poured around all the cardboard pieces. The 1 inch wide piece of Plexiglas was removed leaving a 1 inch gap. This gap was filled with ground up chalk, about 30 grams treated with 3 mL of Formulation H and 3 mL of distilled water. A top piece of Plexiglas was placed on top of the sand, chalk and cardboard, this top piece having a 1 inch diameter hole that is positioned over the bottom piece of cardboard, and the bottom and top pieces of Plexiglas clamped together with binder clips. About 200 worker Eastern subterranean termites (*Rhinotermitidae reticulitermes*) were placed onto the cardboard through the opening in the top piece of Plexiglas. The hole was covered with a plastic Petri dish cover and taped to the Plexiglas. The test arena was stored in a loosely closed black plastic bag at ambient temperature. An untreated control arena was also included in the evaluation. The test and control arenas were examined daily for six days. At day 6 the untreated control arena had termite tunnels through the chalk layer and feeding damage to all pieces of cardboard. The treated arena had termite tunnels up to the treated chalk layer but no tunnels through the chalk layer; feeding damage was limited to the bottom piece of cardboard, indicating a repelling effect.

Example 13

German Cockroach Repellency Assay

A cockroach test arena was prepared by coating the upper edges of a 12 inch wide by 20 inch long by 3 inch high polystyrene tray with a 50/50 mixture of petroleum jelly to keep the cockroaches from escaping. Two sections were cut from a bottom of a cardboard egg carton and inverted to form a cockroach harborage. One section was sprayed with Formulation H and placed at one end of the test arena. The second section was not treated and placed at the opposite end of the arena. Three Smarties® roll candies were placed at the midpoint of the arena as a food source. Fifty adult male German cockroaches (*Blattella germanica*) were placed in the center of the test arena and observed daily for 9 days. This test was run in duplicate. The observation results of which harborage the cockroaches preferred are summarized in the following table.

| | German Cockroach Repellency Results | | | |
|---|---|---|---|---|
| Day of | Number Under Untreated Harborage | | Number Under Treated Harborage | |
| Observation | Replicate 1 | Replicate 2 | Replicate 1 | Replicate 2 |
| 1 | 10 | 27 | 5 | 4 |
| 2 | — | — | 1 | 0 |
| 3 | 27 | 28 | 5 | 5 |
| 4 | 18 | 15 | 3 | 7 |
| 5 | — | — | 4 | 1 |
| 6 | 17 | 16 | 8 | 8 |
| 7 | 12 | 16 | 6 | 3 |
| 8 | 28 | 33 | 1 | 12 |
| 9 | 19 | 24 | 4 | 15 |

As can be seen from the data above, German cockroaches preferred the untreated harborage over the treated harborage, therefore exhibiting repellency.

Example 14

Brown Marmorated Stinkbug Repellency

A test arena was prepared by coating the upper edge of a Tupperware® 6 inch by 8 inch storage container with a 50/50 mixture of petroleum jelly and mineral oil to prevent stinkbugs from escaping. A green bean was dipped into Formulation F and was placed at one end of the arena. An untreated green bean was placed at the other end of the container. Fourteen Brown marmorated stinkbugs ($2^{nd}$ to $4^{th}$ instar, *Pentatomidae halymoropha*) were placed into the center of the arena. A second test arena was prepared as a control using untreated green beans at each end of the container. The test arenas were maintained at ambient temperature for 96 hours, at which time it was observed that in the second test arena (control) stinkbugs fed off both green beans equally while the stinkbugs fed in the container with the treated green bean fed on the untreated green bean only indicating a repelling effect.

Example 15

Repelling Tobacco Bud Worm Moths Egg Deposition on Cotton

Four cotton plants (non BT cotton plants with two true leaves) were treated with Formulation F by placing a single drop of the formulation onto the top surface of each leaf. A treated plant was placed at one side of a BioQuip® Products wire mesh cage (14" by 14" by 14"); an untreated cotton plant was placed at the other end of the cage, four replicates. Five gravid female tobacco budworm moths (*Geometridae helicoverpa*) were introduced into each cage. Sixteen hours after moth introduction the number of eggs deposited on the treated and untreated cotton leaves were counted. The table below summarizes the egg count in the four replicate tests.

| Tobacco Budworm Moth Egg Deposition on Cotton Leaves | | | | | |
|---|---|---|---|---|---|
| | Number Of Eggs Per Plant | | | | |
| Treatment | Rep 1 | Rep 2 | Rep 3 | Rep 4 | Average |
| Formulation F | 3 | 2 | 2 | 7 | 3.5 |
| Control | 27 | 37 | 37 | 54 | 38.8 |

This data indicates that plants treated with oleic acid and methyl anthranilate provide a repellency effect to Tobacco budworm moths when selecting oviposition sites.

Example 16

Repelling Brown Dog Ticks

Formulations H and I were tested for repellency of Brown dog ticks (*Rhipcephalus sanguinensis*) in the following manner:

Five strips of filter paper, 1 inch by 3 inches, were each treated with 1 mL of the test Formulation and were allowed to dry. Untreated strips of filter paper of the same dimensions were stapled to the bottom of each treated strip providing a final test strip 6 inches long. The test strips were suspended vertically over a tray with the untreated portion at the bottom. An additional five test strips were prepared and were untreated to be used as controls. Five mixed sex dog ticks were tested per replicate. One tick at a time was introduced to the untreated part of the test strip and allowed to quest upwards. Ticks were observed for up to one minute to determine if the tick crossed onto the treated filter paper and continued to crawl upward. Any tick that stopped, turned around or dropped off after contacting the treated portion of the test strip was classified as repelled. All 25 ticks were repelled when Formulation H and Formulation I were tested. None of the ticks were repelled in the control tests. These tests indicate that formulations of oleic acid and methyl anthranilate are excellent repellants of Brown dog ticks.

Example 17

Repelling Yellow Fever Mosquito

Formulations H and I were tested for repellency of Yellow Fever mosquito (*Aedes aegypti*) in the following manner:

A mosquito exposure container and membrane feeder was used to present mosquitos with a choice of three bovine blood-filled wells covered with a collagen membrane. The blood was prepared by adding 72 mg of ATP disodium salt to 26 mL of bovine blood as a feeding stimulant. The blood was poured into the wells of the membrane feeder until each well was completely filled (meniscus slightly above the level of the well. Circular pieces of collagen (3 cm in diameter) were placed over each well. One membrane was treated with 25 microliters of Formulation H, one with 25 microliters of Formulation I and one was untreated. Five replicates were tested. The membrane feeder was connected to a heated water bath and warmed to 37° C. to 40° C. The exposure container with 250 female mosquitoes was placed over the feeder and opened and the number of mosquitoes probing the membrane covering each well was recorded every two minutes for a period of 20 minutes. A new batch of female mosquitoes was used for each replicate. The number of probes per replicate was totaled and the totals were averaged. The average number of probes on the control membrane was 65, the average probes on the Formulation H membrane was 0, and the average probes on the membrane treated with Formulation I was 6.8. This data shows that formulations of oleic acid and methyl anthranilate are excellent repellants of Yellow Fever mosquitoes.

Example 18

Repelling Cat Flea Larvae

Formulation H and dilutions thereof were tested for repellency to Cat flea larvae (*Ctenocephalides felis*) in the following manner:

Test solutions of Formulation F were prepared by diluting Formulation F with polyethylene glycol, Formulation F contains 30% by weight oleic acid and 10% by weight methyl anthranilate (40% total active ingredients); the first dilution provided a concentration of 12% active ingredients (Formulation 18-1); the second dilution provided a concentration of 4% active ingredients (Formulation 18-2); the third dilution provided a concentration of 1.2% active ingredients (Formulation 18-3); and the final dilution provided a concentration of 0.4% active ingredients (Formulation 18-4).

A round piece of black construction paper (150 mm diameter) was treated with test solutions of Formulation H by covering half of the paper with aluminum foil prior to spraying the test formulation onto the uncovered half. The treated paper was affixed to the bottom of a 150×15 mm Petri dish base. The Petri plate was allowed to dry in a laboratory fume hood for several minutes. Ten cat flea larvae were released in the median area of the treated paper and were observed to be on the untreated or treated portion of the test paper for 2 to 3 hours. The observations are summarized in the table below.

| Cat Flea Larvae Repellency | | | |
|---|---|---|---|
| Formulation Treatment | Elapsed Time (Hr) | Number Of Larvae in Untreated Area | Number Of Larvae in Treated Area |
| F | 1 | 10 | 0 |
|   | 2 | 10 | 0 |
|   | 2.5 | 10 | 0 |
| 18-1 | 1 | 10 | 0 |
|   | 3 | 9 | 1 |
| 18-2 | 1 | 10 | 0 |
|   | 3 | 10 | 0 |
| 18-3 | 1 | 10 | 0 |
|   | 3 | 10 | 0 |
| 18-4 | 1 | 10 | 0 |
|   | 3 | 10 | 0 |

This data indicates that cat flea larvae are repelled by formulations containing oleic acid and methyl anthranilate at rates as low as 0.4% of the combined active ingredients.

Example 19

Southern Corn Rootworm Repellency

Test A: A test arena was prepared by cutting a piece of round filter paper in half and placing both halves on the bottom of a plastic Petri dish leaving a small gap between the two halves of filter paper. The pieces of filter paper were moistened with 1 mL of deionized water per side. Three germinated corn seedlings were dipped into Formulation F, allowed to dry, and placed at one end of the Petri dish on one piece of filter paper as far as possible from the gap between the pieces of filter paper. Three untreated germinated corn seedlings were placed on the other piece of filter paper as far as possible from the gap. Eighteen second instar Southern corn rootworms (*Diabrotica undecimpunctata howardi*) were placed in the midline gap between the two pieces of filter paper and a plastic Petri lid was placed on top. An untreated control having three untreated germinated corn seedlings at each side was tested as well as a fully treated test where all six germinated corn seedlings were included in the test. The Petri dishes were maintained at ambient temperature and humidity in a dark growth chamber for 24 hours. Observations were made at 4 hours and 24 hours to determine if the larvae were feed in the germinated corn seedlings. These observations are summarized in the table below.

| Southern Corn Rootworm Larvae Feeding Observations | | |
|---|---|---|
| Treatment | Larvae Feeding at 4 Hours | Larvae Feeding at 24 Hours |
| Untreated vs Treated | 9 larvae on untreated corn 0 larvae on treated corn remainder in middle | 12 larvae on untreated corn 0 larvae on treated corn remainder in middle |
| Untreated Control | 6 larvae on each side (12 total) remainder in middle | 6 larvae on one side 12 larvae on the other side remainder in middle |
| Both Sides Treated | 0 feeding All in middle or on edge of filter paper | 1 larvae feeding on corn remainder in middle or edge of filter paper |

This data indicates that Southern corn rootworm larvae are repelled from feeding by formulations containing oleic acid and methyl anthranilate.

Test B: A 50 mL polypropylene conical tube was filled with 20 mL of top soil containing 10% water. About 75 Southern corn rootworm eggs (*Diabrotica undecimpunctata howardi*) were placed onto the soil. The eggs were suspended in distilled water and transferred to the soil with a pipette. A final layer of 10 mL of top soil, for untreated control tests or treated soil for treated tests was added to the top. For treated tests, 375 mg of Formulation F was diluted with 15 mL of distilled water. This solution was added to 150 mL of top soil and mixed thoroughly. Treatments in which treated soil was used for both the bottom layer and top layer were also included. A 1 inch lettuce disk was placed on the top of top layer of soil as bait, the tubes were capped and stored at ambient temperature and humidity for 7 days. The lettuce disks were replaced after 3 days. After 7 days the larvae that had hatched and reached the lettuce disks were counted as well as observing and larvae that had hatched and remained in the soil. Each test was performed in duplicate. The observations made are summarized in the table below.

Southern Corn Rootworm Egg Hatch and Larvae Feeding Observations

| Treatment | Replicate | Observation |
|---|---|---|
| Untreated control | 1 | 44 larvae on lettuce disk |
| | 2 | 63 larvae on lettuce disk |
| Untreated bottom soil, treated top soil | 1 | 0 on lettuce disk Very few eggs hatched |
| | 2 | 0 on lettuce disk Very few eggs hatched |
| Treated bottom soil, treated top soil | 1 | 0 on lettuce disk 0 eggs hatched |
| | 2 | 0 on lettuce disk 0 eggs hatched |

This data indicates that Southern corn rootworm larvae are repelled from feeding by formulations containing oleic acid and methyl anthranilate and that Southern corn rootworm eggs fail to hatch in the presence of oleic acid and methyl anthranilate.

Example 20

Saw-Toothed Grain Beetle Repellency

A round piece of black construction paper (150 mm diameter) was treated with Formulation H by covering half of the paper with aluminum foil prior to spraying the nest formulation onto the uncovered half. The treated paper was affixed to the bottom of a 150×15 mm Petri dish base. The Petri plate was allowed to dry in a laboratory fume hood for several minutes. Fifty Saw-toothed grain beetles (*Oryzaephilus surinamensis*) were released in the median area of the construction paper and were observed to be on the untreated or treated portion of the test paper for several hours. A control test in which one side of the construction paper was sprayed with polyethylene glycol only was also included. The observations are summarized in the table below.

Saw-toothed Grain Beetle Repellency Observations
Saw-Toothed Grain Beetles Observed on Treated or Untreated Paper

| Elapsed Time (Hr) | Treated | Untreated |
|---|---|---|
| Formulation H treatment | | |
| 1 | 5 | 45 |
| 2 | 6 | 44 |
| 3 | 3 | 47 |
| 4.5 | 2 | 48 |
| 5.5 | 2 | 48 |
| 6.5 | 11 | 39 |
| 21.5 | 12 | 38 |
| Control (Polyethylene glycol = Treated) | | |
| 1 | 25 | 25 |
| 2 | 25 | 25 |
| 3 | 30 | 20 |
| 18.5 | 40 | 10 |

This data indicates that a mixture of oleic acid and methyl anthranilate exhibit repellency to Saw-toothed grain beetles.

Example 21

Confused Flour Beetle Repellency

A round piece of black construction paper (150 mm diameter) was treated with Formulation H by covering half of the paper with aluminum foil prior to spraying the test formulation onto the uncovered half. The treated paper was affixed to the bottom of a 150×15 mm Petri dish base. The Petri plate was allowed to dry in a laboratory fume hood for several minutes. Thirty Confused flour beetles (*Tribolium confusum*) were released in the median area of the construction paper and were observed to be on the untreated or treated portion of the test paper for several hours. A control test in which one side of the construction paper was sprayed with polyethylene glycol only was also included. The observations are summarized in the table below.

Confused Flour Beetle Repellency Observations
Confused Flour Beetles On Treated or Untreated Paper

| 10:30 am start | Formulation H | | Polyethylene Glycol (Control) | |
|---|---|---|---|---|
| Time (Hr) | Treated | Untreated | Treated | Untreated |
| 1 | 1 | 29 | — | — |
| 2 | 0 | 30 | — | — |
| 3 | 0 | 30 | — | — |
| 4 | 0 | 30 | 25 | 25 |
| 5 | 0 | 30 | 25 | 25 |
| 6 | 2 | 28 | 30 | 20 |
| 21.5 | 2 | 28 | 40 | 10 |

This data indicates that a mixture of oleic acid and methyl anthranilate exhibit repellency to Confused flour beetles.

Example 22

Small Carpenter Bee Repellency

A residential area that was heavily infested with small carpenter bee nesting holes in the ground (*Apidae caeratina*) was marked off in 4 two foot by two foot test plots. Each test plot contained 24 or more small carpenter bee nesting holes. One of the test plots was treated with Formulation F, one with Formulation 18-1 and one with Formulation 18-2. The remaining test plot was left untreated as a control. The formulations were applied using a hand held spray bottle spraying about 12 inches above the test plot, approximately 24 spray pumps per test plot. The test plots were observed for 8 hours to determine if the small carpenter bees entered the nesting holes or were repelled. The test was performed on a warm day in May 2013. The table below summarizes the observations.

| | Small Carpenter Bee Repellency Observations | | | | | | | |
|---|---|---|---|---|---|---|---|---|
| | Observation Time | | | | | | | |
| Treatment | 10 AM | 11 AM | 12 PM | 1 PM | 2 PM | 3 PM | 4 PM | 5 PM |
| Control | | | | | | | | |
| No. Bees entering Hole | 3 | 4 | 3 | 11 | 4 | 4 | 1 | 0 |
| No. Bees Flying Above Holes | 3 | 7 | 6 | 9 | 11 | 5 | 2 | 0 |
| Formulation 18-2 | | | | | | | | |
| No. Bees entering Hole | 0 | 0 | 0 | 0 | 0 | 0 | 0 | 0 |
| No. Bees Flying Above Holes | 4 | 8 | 10 | 8 | 7 | 3 | 0 | 0 |
| Formulation 18-1 | | | | | | | | |
| No. Bees entering Hole | 0 | 0 | 0 | 1 | 0 | 0 | 0 | 0 |
| No. Bees Flying Above Holes | 2 | 5 | 5 | 10 | 8 | 4 | 1 | 0 |
| Formulation. F | | | | | | | | |
| No. Bees entering Hole | 0 | 0 | 0 | 0 | 0 | 0 | 0 | 0 |
| No. Bees Flying Above Holes | 2 | 2 | 5 | 7 | 9 | 2 | 1 | 0 |

After 28 hours no bees were observed near the treated plots. This data indicates that a mixture of oleic acid and methyl anthranilate exhibit repellency to small carpenter bees.

In addition to the insects mentioned in the foregoing examples the following orders of insects have been repelled by a mixture of oleic acid and methyl anthranilate (Family, Genus):

Hymenoptera—carpenter bee (*Apidae Xylocopa*) and bumblebee (*Apidae Bombus*);

Hemiptera—bed bug (*Cimedae Cimex*);

Diptera—common house mosquito (*Culicidae Anopheles*); house fly (*Muscidae Musca*), flesh fly (*Sarcophagidea Sarcophagi*), fruit flies (*Drosophilidae Drosophila*), phorid flies (*Phoridae Megaselia*);

Lepidroptera—Indian meal moth (*Pyralidae Plodia*);

Araneae—Black widow spider (*Theridiidae Latrodectus*), Brown recluse spider (*Loxoscelidas Loxosceles*), Wolf spider (*Lycosidae*), Daddy long-legs spider (*Pholcidae*);

Tylenchida—Root knot nematode (*Meloidogynidae Meloidogynae*)

Example 23

Assessment of Bird Repellent Activity

Bird repellent activity was tested by treating black oil sunflower seeds with Formulation F diluted by 50% with deionized water. Treatment 1 was prepared by coating black oil sunflower seed with 10 mL of the diluted formulation per kilogram of seed, Treatment 2 was prepared by coating black oil sunflower seed with 50 mL of the diluted formulation per kilogram of seed. Four 20" by 20" wooden trays were suspended from the cross brackets of a Duncraft® Squirrel Stopper System bird feeder and 75 grams of treated seed was placed onto two trays (designated to be used for treated seed only) and 75 grams of untreated seed was placed onto the two remaining trays as controls. The trays were monitored daily for birds feeding on the seed. After each day the remaining seed was collected for weighing and replaced with new seed. The tray positions were moved by one position every time they were refilled to eliminate positional effects caused by the birds favoring certain locations of the feeder over other positions. The tests were run for two weeks per treatment, 4 replicates per treatment. There was no statistical difference between the amount of treated seed consumed and the amount of untreated seed consumed. Birds observed feeding on the seed include Turtle dove, House finch, American goldfinch, Downey woodpecker, Harry woodpecker, Northern flicker, Red bellied woodpecker, Blue jay, Carolina chickadee, Tufted titmouse, Carolina wren, Grey catbird, European starling, House sparrow, Cardinal and Common grackle.

Example 24

Repelling Yellow Fever Mosquito

A mixture of 3.0 grams of oleic acid, 1.0 gram of methyl anthralinate and 96.0 grams of isopropyl alcohol was stirred until homogenous. This formulation was labeled Ex. 24. For comparative purposes a 5% solution of N,N-diethyl-3-methylbenzamide in isopropyl alcohol (active ingredient in DEET Insect Repellant) was also tested. This sample was labeled 5% DEET. Isopropyl alcohol (IPA), water and untreated collagen membranes were also tested.

An in vitro laboratory trial was conducted to evaluate the repellency of a test formulation aged at various intervals against female *Aedes aegypti*. 250 female adult mosquitoes, *Aedes aegypti*, were used per replicate (5 replicates per test). Adult mosquitoes were 6 days old and were deprived of sucrose solution for approximately 18 hours prior to testing. An exposure container was used to present the mosquitoes with a choice of five blood-filled wells covered with collagen membranes. The collagen membranes were treated by pipetting 25 µL of the test formulation or solvent onto the appropriate membrane and spreading it evenly with the tip of the pipette. The membranes were left to age undisturbed at ambient temperature and humidity for 2 hours.

The exposure container used was a 30.5 cm×30.5 cm×30.5 cm rigid plastic frame supported by four, 4-cm high legs, with a sleeved entry on one side and a sliding door on the bottom.

The membrane feeder consisted of five wells (3 cm in diameter×8 mm in depth) in line on a hollow plastic block (6 cm wide×22 cm long×3 cm deep), which fits through the sliding door in the bottom of the exposure container. Hoses attached to each side of the block circulate heated water that is pumped from a water bath. The sliding door in the bottom of the exposure container covers and uncovers the wells in the membrane feeder, allowing mosquitoes to access the wells.

The membrane feeder was connected to a heated water bath, and warm water passed through the feeder via a circulating pump so that the wells were warmed to 89-95° F. Seventy-two (72) mg of ATP (disodium salt) were added to 26 mL of warmed citrated bovine blood, which was poured into the wells until they were completely full. The collagen membranes, after being treated and aged as described above, were placed over each of the wells, completely covering the blood. Care was taken to eliminate all air bubbles from between the membrane and the surface of the blood.

The mosquitoes were released into the exposure container just prior to exposure to the membranes. After the five minutes, the exposure container was placed on the membrane feeder and the sliding door opened, allowing the mosquitoes to access the wells. The number of mosquitoes probing each membrane was recorded every two minutes for twenty minutes.

The above procedures were repeated until five replicates were completed. A new batch of 250 female mosquitoes and fresh blood were used for each replicate, and the wells were cleaned in between replicates. The position of the treatments was rotated for each replicate, so that each treatment was tested on each of the five wells.

The data from the five replicates are presented below.

| Replicate 1 | | | | | |
|---|---|---|---|---|---|
| Time (min) | Ex. 24 | 5% DEET | IPA | Water | Untreated |
| 2 | 0 | 0 | 1 | 1 | 0 |
| 4 | 0 | 3 | 9 | 4 | 1 |
| 6 | 0 | 5 | 8 | 7 | 3 |
| 8 | 1 | 7 | 19 | 13 | 2 |
| 10 | 2 | 10 | 12 | 15 | 9 |
| 12 | 7 | 14 | 15 | 14 | 13 |
| 14 | 8 | 16 | 15 | 16 | 15 |
| 16 | 9 | 16 | 18 | 23 | 15 |
| 18 | 6 | 15 | 18 | 16 | 17 |
| 20 | 5 | 12 | 16 | 17 | 19 |
| Total | 38 | 98 | 131 | 126 | 94 |

| Replicate 2 | | | | | |
|---|---|---|---|---|---|
| Time (min) | Untreated | Ex. 24 | 5% DEET | IPA | Water |
| 2 | 0 | 0 | 2 | 7 | 4 |
| 4 | 12 | 1 | 5 | 13 | 6 |
| 6 | 12 | 2 | 8 | 20 | 13 |
| 8 | 14 | 3 | 6 | 18 | 15 |
| 10 | 19 | 6 | 6 | 21 | 17 |
| 12 | 27 | 13 | 6 | 11 | 16 |
| 14 | 13 | 9 | 4 | 14 | 11 |
| 16 | 16 | 9 | 5 | 15 | 10 |
| 18 | 18 | 8 | 7 | 15 | 9 |
| 20 | 21 | 6 | 8 | 11 | 9 |
| Total | 152 | 57 | 57 | 145 | 110 |

| Replicate 3 | | | | | |
|---|---|---|---|---|---|
| Time (min) | Water | Untreated | Ex. 24 | 5% DEET | IPA |
| 2 | 13 | 14 | 6 | 3 | 12 |
| 4 | 15 | 16 | 5 | 6 | 15 |
| 6 | 23 | 15 | 4 | 5 | 13 |
| 8 | 16 | 18 | 3 | 7 | 13 |
| 10 | 14 | 16 | 3 | 7 | 9 |
| 12 | 12 | 15 | 3 | 6 | 10 |
| 14 | 11 | 18 | 4 | 5 | 6 |
| 16 | 18 | 18 | 5 | 9 | 12 |
| 18 | 16 | 15 | 8 | 5 | 9 |
| 20 | 17 | 14 | 1 | 8 | 7 |
| Total | 155 | 159 | 42 | 61 | 106 |

| Replicate 4 | | | | | |
|---|---|---|---|---|---|
| Time (min) | IPA | Water | Untreated | Ex. 24 | 5% DEET |
| 2 | 2 | 5 | 3 | 0 | 1 |
| 4 | 12 | 4 | 6 | 0 | 0 |
| 6 | 6 | 5 | 8 | 0 | 0 |
| 8 | 14 | 9 | 8 | 0 | 0 |
| 10 | 9 | 9 | 8 | 1 | 0 |
| 12 | 13 | 8 | 6 | 0 | 0 |
| 14 | 11 | 11 | 4 | 0 | 0 |
| 16 | 15 | 8 | 5 | 0 | 0 |
| 18 | 10 | 9 | 2 | 0 | 0 |
| 20 | 9 | 7 | 3 | 0 | 0 |
| Total | 101 | 75 | 53 | 1 | 1 |

| Replicate 5 | | | | | |
|---|---|---|---|---|---|
| Time (min) | 5% DEET | IPA | Water | Untreated | Ex. 24 |
| 2 | 5 | 7 | 7 | 4 | 1 |
| 4 | 3 | 13 | 13 | 6 | 2 |
| 6 | 8 | 20 | 10 | 13 | 1 |
| 8 | 10 | 23 | 18 | 13 | 3 |
| 10 | 16 | 21 | 21 | 15 | 2 |
| 12 | 20 | 21 | 18 | 11 | 5 |
| 14 | 13 | 19 | 22 | 18 | 5 |
| 16 | 15 | 18 | 19 | 20 | 1 |
| 18 | 11 | 23 | 17 | 20 | 2 |
| 20 | 18 | 23 | 14 | 14 | 1 |
| Total | 119 | 188 | 159 | 134 | 23 |

| Average of 5 Replicates | | | | | |
|---|---|---|---|---|---|
| Treatment | Ex. 24 | DEET | IPA | Water | Untreated |
| Total Probes | 32.2 | 67.2 | 134.2 | 125.0 | 118.4 |

The above results show that the composition of the present invention provides superior repellency than does DEET.

The foregoing should only be considered as illustrative of the principles of the invention. Further, since numerous modifications and changes may readily occur to those skilled in the art, it is not desired to limit the invention to the exact compositions of components and materials as described herein, and accordingly, all suitable modifications and equivalents may be resorted to, falling within the scope of the claimed invention.

What is claimed is:

1. A composition comprising an insect or acarid repellant amount of a composition comprising: (a) an anthranilate ester; and (b) a fatty acid, wherein: (1) the composition excludes fatty acid salt; (2) the weight ratio of fatty acid to anthranilate ester is from 1:10 to 20:1; and (3) the composition does not repel birds.

2. The composition of claim 1 wherein said anthranilate ester is selected from the group consisting of dimethyl anthranilate, methyl anthranilate, ethyl anthranilate, phenylethyl anthranilate and menthyl anthranilate.

3. The composition of claim 1 wherein said anthranilate ester is methyl anthranilate or dimethyl anthranilate.

4. The composition of claim 1 wherein said fatty acid is selected from the group consisting of saturated and unsaturated fatty acids containing from 8 to 24 carbon atoms.

5. The composition of claim 4 wherein said fatty acid contains from 13 to 21 carbon atoms.

6. The composition of claim 1 wherein said fatty acid is selected from the group consisting of oleic acid, ricinoleic acid, linoleic acid, palmitic acid and stearic acid.

7. The composition of claim 1 wherein the fatty acid is oleic acid.

8. The composition of claim 1 wherein the weight ratio of fatty acid to anthranilate ester is from 1:5 to 10:1.

9. The composition of claim 1 wherein the weight ratio of fatty acid to anthranilate ester is from 1:1 to 5:1.

10. The composition of claim 1 wherein the composition further comprises a solvent.

11. The composition of claim 10, wherein the solvent is selected from a $C_1$-$C_4$ alcohol, an ester, a ketone, a petroleum distillate or a glycol.

12. The composition of claim 1, wherein the composition further comprises an antioxidant preservative agent.

13. A method of repelling an insect or acarid pest comprising applying the composition of claim 1 to a locus where such repelling is desired.

14. The method of claim 13 wherein said pest is selected from the group consisting of Hymenoptera, Blattodea, Hemiptera, Diptera, Coleoptera, Lepidoptra, and ticks.

15. The method of claim 13 wherein said pest is selected from the group consisting of pavement ant, carpenter ant, Argentine ant, little fire ant, ghost ant, cold tolerant ant, wood ant, Asian needle ant, odorus ant, rover ant, fire ant, bigheaded ant, honeybee, carpenter bee, bumble bee, small carpenter bee, European paper wasp, German yellowjacket and bald-faced hornet, German roach, Eastern subterranean termite, bed bugs, brown marmorated stink bugs, Aedes and Anopheles mosquitoes, corn rootworm, sawtoothed beetle, confused flour beetle, tobacco budworm and brown dog tick.

* * * * *